United States Patent
Silvestrini et al.

(10) Patent No.: US 9,216,107 B2
(45) Date of Patent: *Dec. 22, 2015

(54) OCULAR IMPLANT DELIVERY SYSTEMS AND METHODS

(71) Applicant: Transcend Medical, Inc., Menlo Park, CA (US)

(72) Inventors: Thomas A. Silvestrini, Alamo, CA (US); Richard S. Lilly, Menlo Park, CA (US)

(73) Assignee: Transcend Medical, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/591,587

(22) Filed: Jan. 7, 2015

(65) Prior Publication Data

US 2015/0126809 A1 May 7, 2015

Related U.S. Application Data

(63) Continuation of application No. 14/165,178, filed on Jan. 27, 2014, now Pat. No. 8,932,205, which is a continuation of application No. 13/721,941, filed on Dec. 20, 2012, now Pat. No. 8,636,647, which is a continuation of application No. 12/753,494, filed on Apr. 2, 2010, now Pat. No. 8,337,393.

(60) Provisional application No. 61/166,574, filed on Apr. 3, 2009.

(51) Int. Cl.
*A61F 9/00* (2006.01)
*A61B 1/07* (2006.01)
*A61B 1/04* (2006.01)
*A61F 9/007* (2006.01)
*A61F 9/008* (2006.01)
*A61B 1/00* (2006.01)
*A61B 1/06* (2006.01)

(52) U.S. Cl.
CPC ............ *A61F 9/0017* (2013.01); *A61B 1/00165* (2013.01); *A61B 1/04* (2013.01); *A61B 1/06* (2013.01); *A61B 1/07* (2013.01); *A61F 9/008* (2013.01); *A61F 9/00781* (2013.01); *A61F 2220/0033* (2013.01)

(58) Field of Classification Search
CPC ..... A61B 1/07; A61B 1/04; A61F 2220/0033
See application file for complete search history.

(56) References Cited

U.S. PATENT DOCUMENTS

| 4,782,819 A | 11/1988 | Adair |
| 4,848,323 A | 7/1989 | Marijnissen et al. |

(Continued)

FOREIGN PATENT DOCUMENTS

WO    WO-2006/099738 A1    9/2006

*Primary Examiner* — WB Perkey
(74) *Attorney, Agent, or Firm* — Fred C. Hernandez; Mintz Levin Cohn Ferris Glovsky and Popeo, P.C.

(57) ABSTRACT

Described herein are delivery devices and methods of using the devices for delivering an ocular implant into a suprachoroidal space without use of a goniolens. The delivery device includes a handle including a channel extending from a proximal end of the handle to a distal end of the handle, an applier coupled to the handle, the applier including a blunt distal tip and an elongate, flexible wire insertable through a fluid channel of an ocular implant, and a fiber optic image bundle reversibly inserted through the channel such that the fiber optic image bundle extends to a region proximal to the blunt distal tip of the applier.

16 Claims, 15 Drawing Sheets

(56) References Cited

U.S. PATENT DOCUMENTS

| | | | |
|---|---|---|---|
| 5,735,792 A | 4/1998 | Vanden Hoek et al. | |
| 5,893,837 A * | 4/1999 | Eagles et al. | 604/9 |
| 6,007,333 A | 12/1999 | Callan et al. | |
| 6,203,513 B1 * | 3/2001 | Yaron et al. | 604/9 |
| 6,258,083 B1 | 7/2001 | Daniel et al. | |
| 7,186,232 B1 * | 3/2007 | Smedley et al. | 604/8 |
| 7,214,223 B2 | 5/2007 | Mueller et al. | |
| 8,167,939 B2 | 5/2012 | Silvestrini et al. | |
| 8,337,393 B2 * | 12/2012 | Silverstrini et al. | 600/104 |
| 8,636,647 B2 * | 1/2014 | Silvestrini et al. | 600/104 |
| 8,932,205 B2 * | 1/2015 | Silvestrini et al. | 600/104 |
| 2002/0133168 A1 * | 9/2002 | Smedley et al. | 606/108 |
| 2003/0093084 A1 * | 5/2003 | Nissan et al. | 606/108 |
| 2006/0155300 A1 * | 7/2006 | Stamper et al. | 606/107 |
| 2007/0191863 A1 | 8/2007 | De Juan et al. | |
| 2009/0182421 A1 * | 7/2009 | Silvestrini et al. | 623/6.13 |
| 2010/0274258 A1 | 10/2010 | Silvestrini et al. | |
| 2010/0280317 A1 | 11/2010 | Silvestrini et al. | |
| 2011/0112546 A1 | 5/2011 | Juan, Jr. et al. | |
| 2011/0224489 A1 | 9/2011 | Deal et al. | |
| 2012/0016286 A1 | 1/2012 | Silvestrini et al. | |
| 2012/0022429 A1 | 1/2012 | Silvestrini et al. | |

* cited by examiner

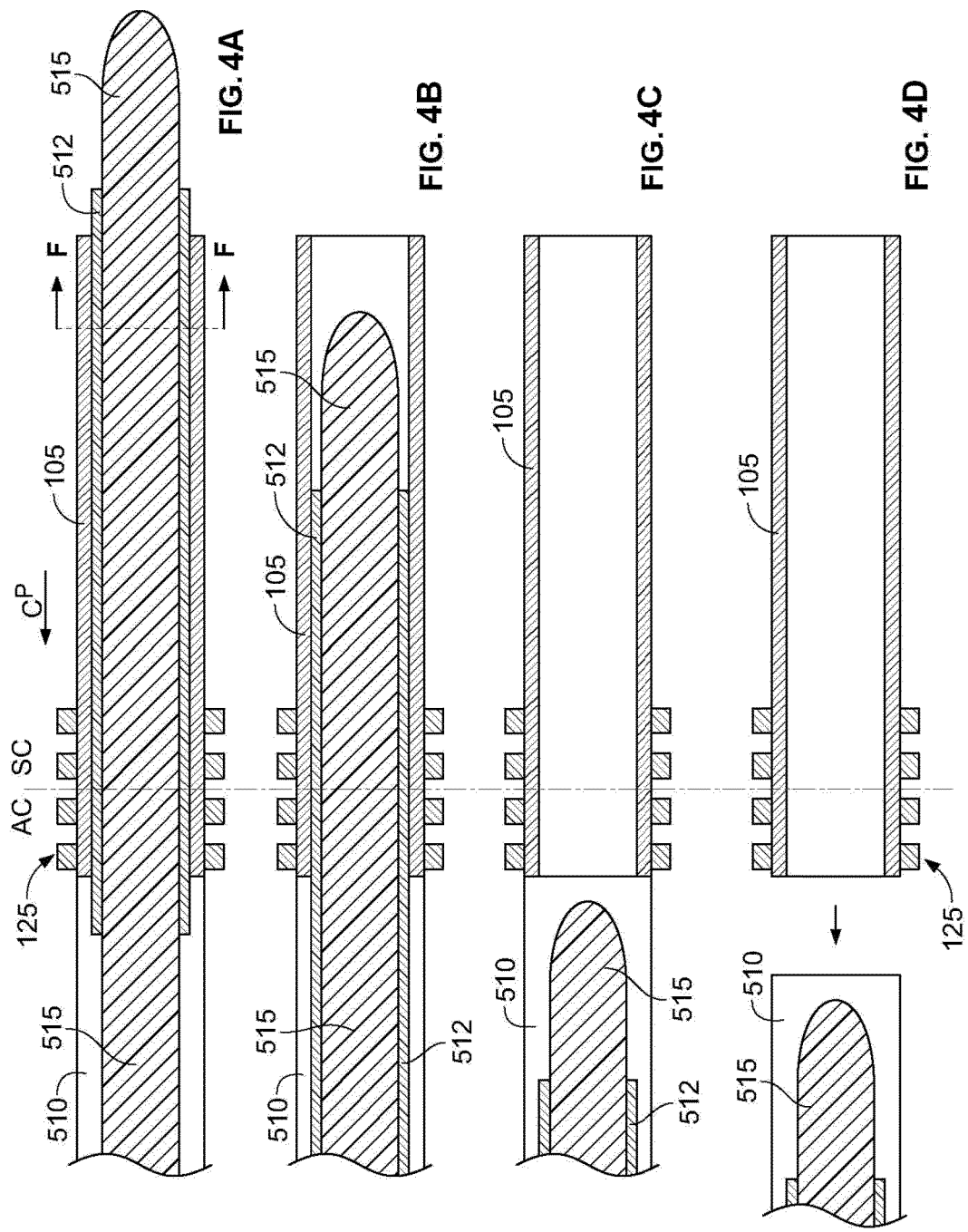

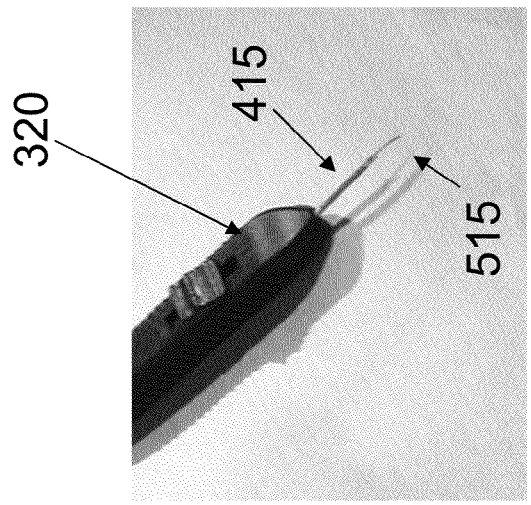
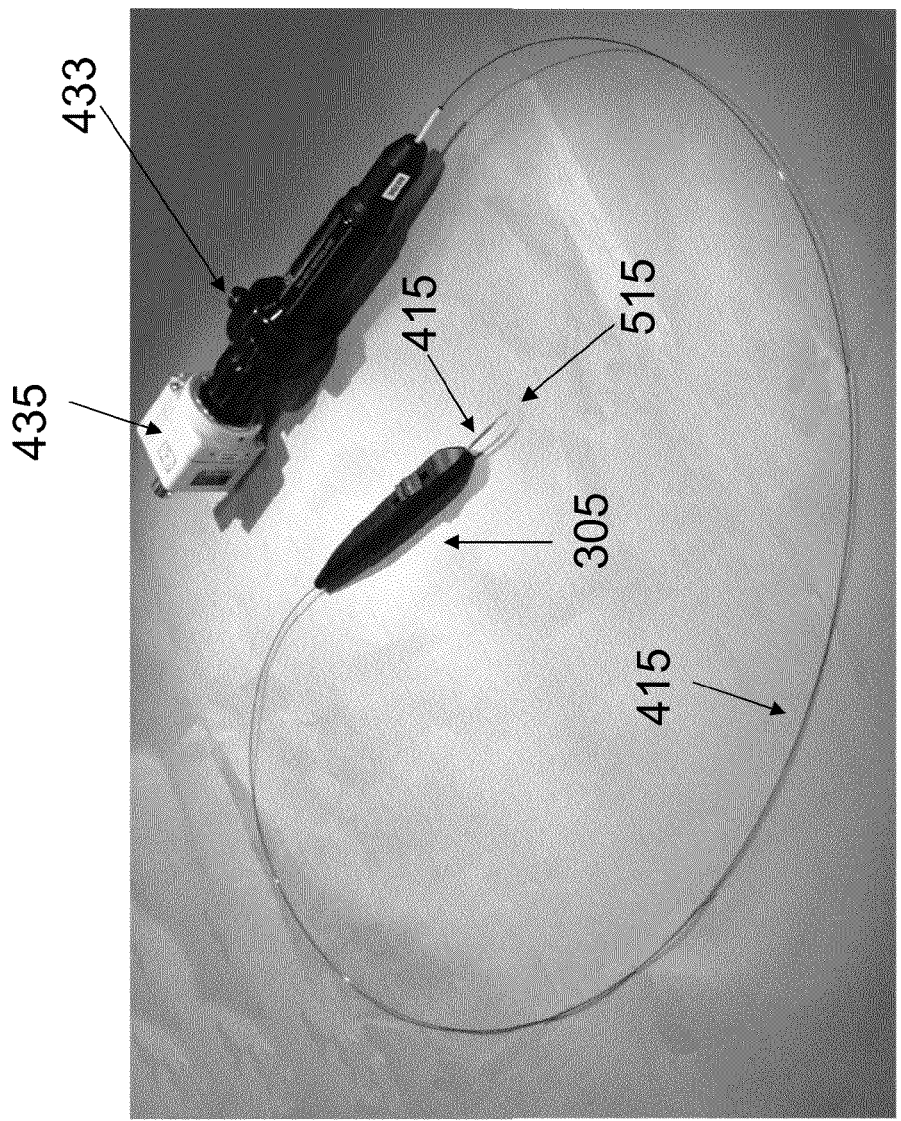

OCULAR IMPLANT DELIVERY SYSTEMS AND METHODS

REFERENCE TO PRIORITY DOCUMENT

This application is a continuation of U.S. patent application Ser. No. 14/165,178, filed Jan. 27, 2014, titled, "Ocular Implant Delivery Systems and Methods;" which in turn claims priority U.S. patent application Ser. No. 13/721,941, now U.S. Pat. No. 8,636,647, filed Dec. 20, 2012, titled, "Ocular Implant Delivery Systems and Methods;" which in turn claims priority to U.S. patent application Ser. No. 12/753,494, now U.S. Pat. No. 8,337,393, filed Apr. 2, 2010, titled, "Ocular Implant Delivery Systems and Methods;" which in turn claims priority to U.S. Provisional Patent Application Ser. No. 61/166,574, filed Apr. 3, 2009, and entitled "Ocular Implant Delivery Systems and Methods." The priority of the filing date of Apr. 3, 2009 is hereby claimed, and the disclosures of each of the abovementioned patent applications are hereby incorporated by reference in their entirety.

BACKGROUND

This disclosure relates generally to methods and devices for use in delivery of devices for the treatment of glaucoma. The mechanisms that cause glaucoma are not completely known. It is known that glaucoma results in abnormally high pressure in the eye, which leads to optic nerve damage. Over time, the increased pressure can cause damage to the optic nerve, which can lead to blindness. Treatment strategies have focused on keeping the intraocular pressure down in order to preserve as much vision as possible over the remainder of the patient's life.

Past treatment includes the use of drugs that lower intraocular pressure through various mechanisms. The glaucoma drug market is an approximate two billion dollar market. The large market is mostly due to the fact that there are not any effective surgical alternatives that are long lasting and complication-free. Unfortunately, drug treatments need much improvement, as they can cause adverse side effects and often fail to adequately control intraocular pressure. Moreover, patients are often lackadaisical in following proper drug treatment regimens, resulting in a lack of compliance and further symptom progression.

With respect to surgical procedures, one way to treat glaucoma is to implant a drainage device in the eye. The drainage device functions to drain aqueous humor from the anterior chamber and thereby reduce the intraocular pressure. The drainage device is typically implanted using an invasive surgical procedure. Pursuant to one such procedure, a flap is surgically formed in the sclera. The flap is folded back to form a small cavity and the drainage device is inserted into the eye through the flap. Such a procedure can be quite traumatic as the implants are large and can result in various adverse events such as infections and scarring, leading to the need to re-operate.

Current devices and procedures for treating glaucoma have disadvantages and only moderate success rates. The procedures are very traumatic to the eye and also require highly accurate surgical skills, such as to properly place the drainage device in a proper location. In addition, the devices that drain fluid from the anterior chamber to a subconjunctival bleb beneath a scleral flap are prone to infection, and can occlude and cease working. This can require re-operation to remove the device and place another one, or can result in further surgeries.

Methods are known in the art for delivering an implant within the eye. Generally, the methods include providing an elongate applier having at its distal region a piercing member or applier intended to pass through tissues of the eye. The distal end of the applier is positioned within the lumen of the implant to be delivered and is advanced to deliver the implant to the target location. The connection between the applier and the implant poses some challenges. The connection needs to be releasable in order to deliver the implant at the target location. The connection also needs to be strong enough so as not to inadvertently release the implant from the end of the applier. Delivery mechanisms intended to release the implant into a target location of the eye can be bulky and require the procedure to be performed "blind," for example, due to higher profiles of the release mechanism used.

SUMMARY

There is a need for improved devices and methods for the treatment of eye diseases such as glaucoma. In particular, there is a need for simplified, low profile devices for the treatment of glaucoma and other diseases using a minimally-invasive delivery system and procedure.

In a first embodiment, disclosed herein is a system for delivering an ocular implant having a fluid channel. The system includes a delivery device and a fiber optic image bundle. The delivery device includes a handle component having a proximal end, a distal end, and a channel extending therethrough. The delivery device also includes an applier coupled to the handle having an elongate, flexible wire insertable through the fluid channel of the ocular implant. The fiber optic image bundle is reversibly insertable through the channel such that the fiber optic image bundle extends to a region proximal to a distal tip of the applier.

The system can further include an illumination source that emits infrared light including an infrared LED and an infrared flood lamp. The illumination source can be external to the fiber optic image bundle. The system can further include a second illumination source. The second illumination source can emit visible light including white incandescent light, white LED and fiberoptic white light. The system can further include a first mechanism configured to control the first illumination source and a second mechanism configured to control the second illumination source. The second illumination source control mechanism adjusts the second illumination source independent of the first illumination source control mechanism and the first illumination source. The system can further include a narrow band pass filter.

The system can further include an imaging device configured to capture image data in the form of video images, still images or both. The imaging device can include a hand-held digital microscope, a digital camera, a CCD video camera, a low mass camera, or a CMOS chip. The imaging device can communicate the image data to a digital projector configured to project images in real-time to a small projector screen displayed near a patient's eye. The region proximal to the distal tip of the applier can be between about 3 and 20 millimeters proximal to the distal tip of the applier. The fiber optic image bundle can further include one or more lenses. The fiber optic image bundle can provide an objective angle view of at least about 65 degrees.

The system can further include an elongate member having a flow pathway, at least one inflow port communicating with the flow pathway, and an outflow port communicating with the flow pathway, wherein the elongate member is adapted to be positioned in an eye such that the inflow port communicates with an anterior chamber and the outflow port communicates with a suprachoroidal space. The system can be used to position the elongate member into a suprachoroidal space without use of a goniolens.

Also described herein are methods of implanting an ocular device into the eye. In an embodiment, disclosed is a method including loading an implant having a fluid passageway onto a delivery device having an applier and a handle component having a channel. The distal end of the fiber optic image bundle is positioned proximal to a distal end of the applier. The method also includes feeding a fiber optic image bundle through the channel, forming an incision in the cornea of the eye, inserting the implant loaded on the applier through the incision into an anterior chamber of the eye, passing the implant along a pathway from the anterior chamber into a suprachoroidal space, positioning at least a portion of the implant into the suprachoroidal space such that a first portion of the fluid passageway communicates with the anterior chamber and a second portion of the fluid passageway communicates with the suprachoroidal space to provide a fluid passageway between the suprachoroidal space and the anterior chamber, and removing the implant from the applier.

The method also can include reversibly inserting the distal end of the fiber optic image bundle through the channel of the handle component to a position proximal to the distal end of the applier. Feeding the fiber optic image bundle can include reversibly inserting the distal end of the fiber optic image bundle through the channel of the handle component to a position between about 3-20 millimeters proximal to the distal end of the applier. Feeding the fiber optic image bundle can include reversibly inserting the distal end of the fiber optic image bundle through the channel of the handle component to about 6 millimeters proximal to the distal end of the applier. The fiber optic image bundle can be less than about 0.5 millimeters in diameter.

Inserting the implant loaded on the applier through the incision into the anterior chamber of the eye can include inserting the implant loaded on the applier and the fiber optic image bundle through a single incision in the cornea into the anterior chamber of the eye. Forming an incision can include forming an incision that is a self-sealing incision. Passing the implant along a pathway from the anterior chamber into the suprachoroidal space can include bluntly dissecting between a tissue boundary of a region of the sclera and a tissue boundary of a region of a ciliary body. The applier can further include a retention layer surrounding an outer surface of the applier comprised of a compliant polymer providing a reversible interference fit between the applier and the implant.

The method can include providing an illumination source to illuminate the eye during implantation, wherein the illumination source is external to the fiber optic image bundle and can emit infrared light. The method can include providing a second illumination source to illuminate the eye during implantation, wherein the second illumination source emits white light. The second illumination source can be adjusted independently of the first illumination source.

Other features and advantages should be apparent from the following description of various embodiments, which illustrate, by way of example, the principles of the described subject matter.

BRIEF DESCRIPTION OF THE DRAWINGS

FIGS. 4A-4D show an exemplary mechanism for delivering an implant into the eye.

FIGS. 5A-5D show a fiber optic visualization and delivery system according to one embodiment.

It should be appreciated that the drawings herein are exemplary only and are not meant to be to scale.

DETAILED DESCRIPTION

There is a need for improved methods and devices for the treatment of eye diseases. In particular, there is a need for low profile, simplified delivery devices that can be used to deliver implants or other devices as well as drugs and other therapeutic material into the eye for the treatment of glaucoma and other diseases. The delivery devices described herein deliver an implant using an applier that can gently and bluntly dissect between tissue margins or tissue layer boundaries, for example, between the iris root and the scleral spur or the iris root part of the ciliary body and the scleral spur into the supraciliary space. The applier of the delivery devices described herein may further dissect between the sclera and the choroid into the suprachoroidal space in the eye. The applier can penetrate certain tissues and separate tissue boundaries while avoid penetrating certain other tissues. The delivery device described herein can include a readily reversible, low-profile, internal retention system between the applier and the implant such that the implant can be delivered to the target location in the eye and avoid inadvertent release of the implant during delivery. The delivery devices described herein also can include a low profile visualization system and illumination system for use during implantation.

Figure 1:
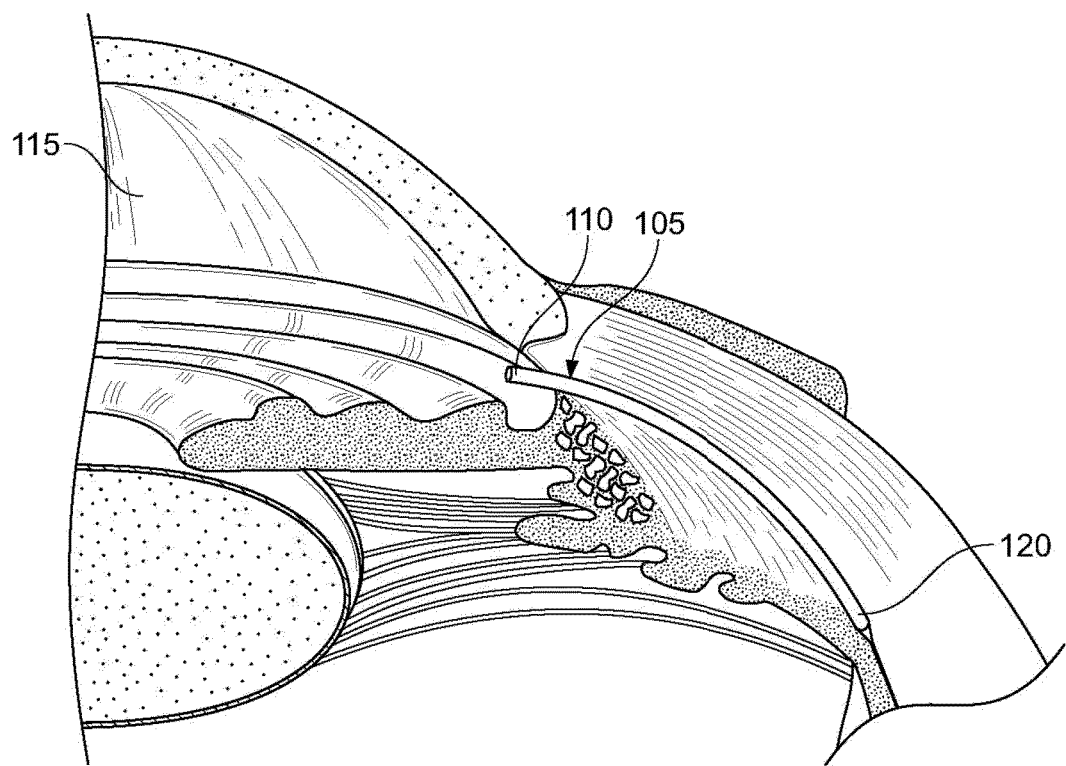
FIG. 1 is a cross-sectional, perspective view of a portion of the eye showing the anterior and posterior chambers of the eye.

FIG. 1 is a cross-sectional, perspective view of a portion of the eye showing the anterior and posterior chambers of the eye. A schematic representation of an implant 105 is positioned inside the eye such that a proximal end 110 is located in the anterior chamber 115 and a distal end 120 extends to a region of the eye that is between the ciliary body and the sclera. Alternatively, the distal end 120 can extend to a region of the eye that is posterior to the ciliary body, such as between the choroid and the sclera. The suprachoroidal space (sometimes referred to as the perichoroidal space) can include the region between the sclera and the choroid. The suprachoroidal space can also include the region between the sclera and the ciliary body. In this regard, the region of the suprachoroidal space between the sclera and the ciliary body may sometimes be referred to as the supraciliary space. The implants described herein are not necessarily positioned between the choroid and the sclera. The implants may be positioned at least partially between the ciliary body and the sclera or may be at least partially positioned between the sclera and the choroid. In any event, the implant can provide a fluid pathway for flow of aqueous humor through or along the implant between the anterior chamber and the suprachoroidal space.

In an embodiment, the implant 105 is an elongate element having one or more internal lumens through which aqueous humor can flow from the anterior chamber 115 into the suprachoroidal space. The implant 105 can have a substantially uniform diameter along its entire length, although the shape of the implant 105 can vary along its length (either before or after insertion of the implant), as described below. Moreover, the implant 105 can have various cross-sectional shapes (such as a, circular, oval or rectangular shape) and can vary in cross-sectional shape moving along its length. The cross-sectional shape can be selected to facilitate easy insertion into the eye. The following applications describe exemplary implants and are incorporated by reference in their entirety: U.S. Patent Publication No. 2007-0191863 and U.S. Patent Application Serial No. 2009-0182421.

Eye Anatomy and Glaucoma

Figure 2:
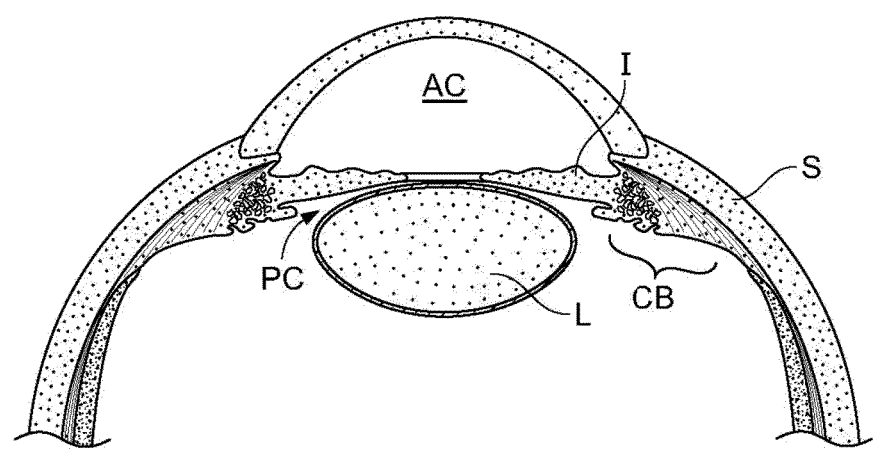
FIG. 2 is a cross-sectional view of a human eye.

FIG. 2 is a cross-sectional view of a portion of the human eye. The eye is generally spherical and is covered on the outside by the sclera S. The retina lines the inside posterior half of the eye. The retina registers the light and sends signals to the brain via the optic nerve. The bulk of the eye is filled and supported by the vitreous body, a clear, jelly-like substance. The elastic lens L is located near the front of the eye. The lens L provides adjustment of focus and is suspended within a capsular bag from the ciliary body CB, which contains the muscles that change the focal length of the lens. A volume in front of the lens L is divided into two by the iris I, which controls the aperture of the lens and the amount of light striking the retina. The pupil is a hole in the center of the iris I through which light passes. The volume between the iris I and the lens L is the posterior chamber PC. The volume between the iris I and the cornea is the anterior chamber AC. Both chambers are filled with a clear liquid known as aqueous humor.

The ciliary body CB continuously forms aqueous humor in the posterior chamber PC by secretion from the blood vessels. The aqueous humor flows around the lens L and iris I into the anterior chamber and exits the eye through the trabecular meshwork TM, a sieve-like structure situated at the corner of the iris I and the wall of the eye (the corner is known as the iridocorneal angle). Some of the aqueous humor filters through the trabecular meshwork near the iris root into Schlemm's canal, a small channel that drains into the ocular veins. A smaller portion rejoins the venous circulation after passing through the ciliary body and eventually through the sclera (the uveoscleral route).

Glaucoma is a disease wherein the aqueous humor builds up within the eye. In a healthy eye, the ciliary processes secrete aqueous humor, which then passes through the angle between the cornea and the iris. Glaucoma appears to be the result of clogging in the trabecular meshwork. The clogging can be caused by the exfoliation of cells or other debris. When the aqueous humor does not drain properly from the clogged meshwork, it builds up and causes increased pressure in the eye, particularly on the blood vessels that lead to the optic nerve. The high pressure on the blood vessels can result in death of retinal ganglion cells and eventual blindness.

Closed angle (acute) glaucoma can occur in people who were born with a narrow angle between the iris and the cornea (the anterior chamber angle). This is more common in people who are farsighted (they see objects in the distance better than those which are close up). The iris can slip forward and suddenly close off the exit of aqueous humor, and a sudden increase in pressure within the eye follows.

Open angle (chronic) glaucoma is by far the most common type of glaucoma. In open angle glaucoma, the iris does not block the drainage angle as it does in acute glaucoma. Instead, the fluid outlet channels within the wall of the eye gradually narrow with time. The disease usually affects both eyes, and over a period of years the consistently elevated pressure slowly damages the optic nerve.

As shown in FIG. 1, the implant 105 can be an elongate member having a proximal end, a distal end, and a structure that permits fluid (such as aqueous humor) to flow along the length of the implant such as through or around the implant from the anterior chamber to the suprachoroidal space. The implant 105 can include at least one internal lumen having at least one opening for ingress of fluid. In addition to serving as a passageway for the flow of aqueous humor through the implant 105 directly from the anterior chamber to the suprachoroidal space, the internal lumen of the implant can be used as an access location to mount the implant 105 onto a delivery system, as described in more detail below. The internal lumen can also be used as a pathway for flowing irrigation fluid into the eye generally for flushing or to maintain pressure in the anterior chamber, or using the fluid to hydraulically create a dissection plane into or within the suprachoroidal space as will be discussed in more detail below.

Delivery System

Figure 3A:
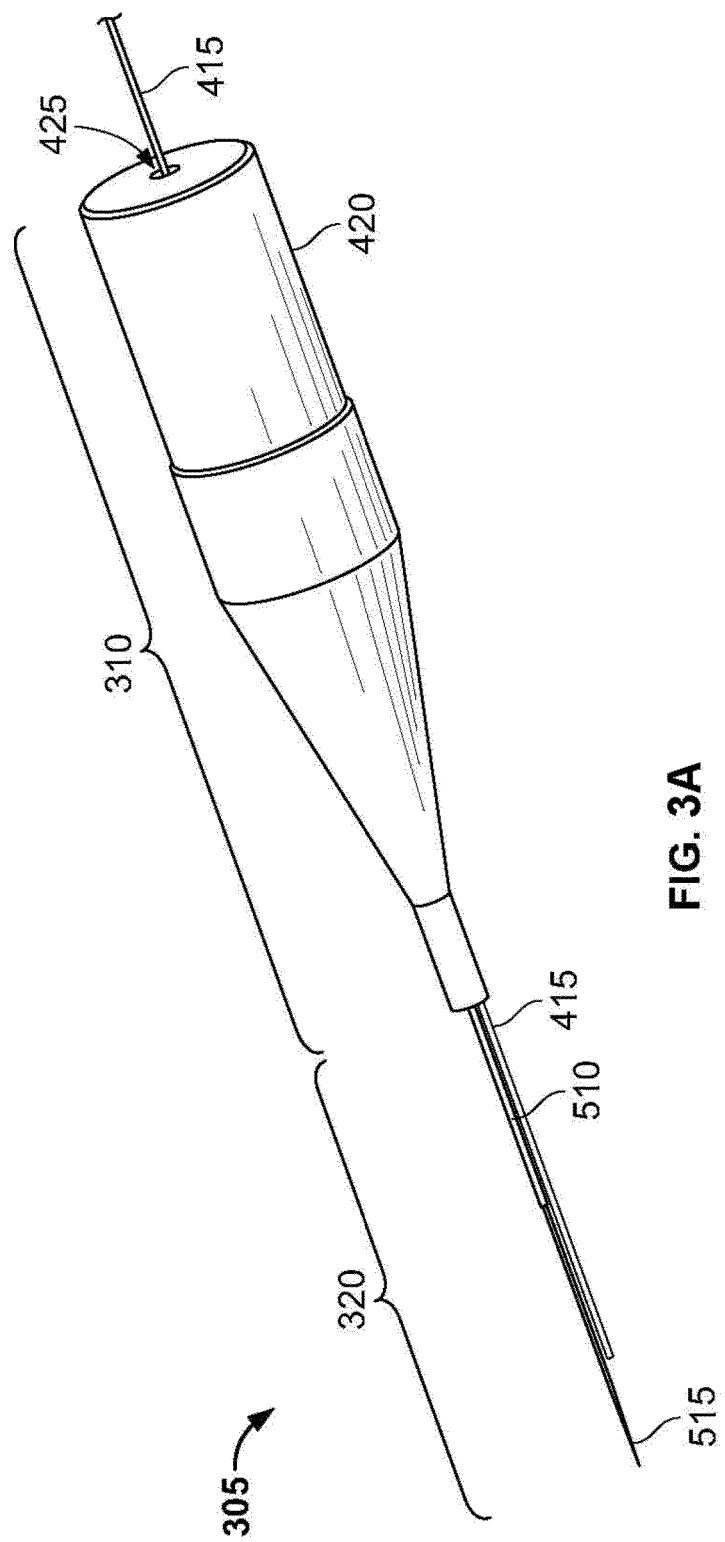
FIG. 3A shows an exemplary delivery system that can be used to deliver an implant into the eye.
Figure 3B:
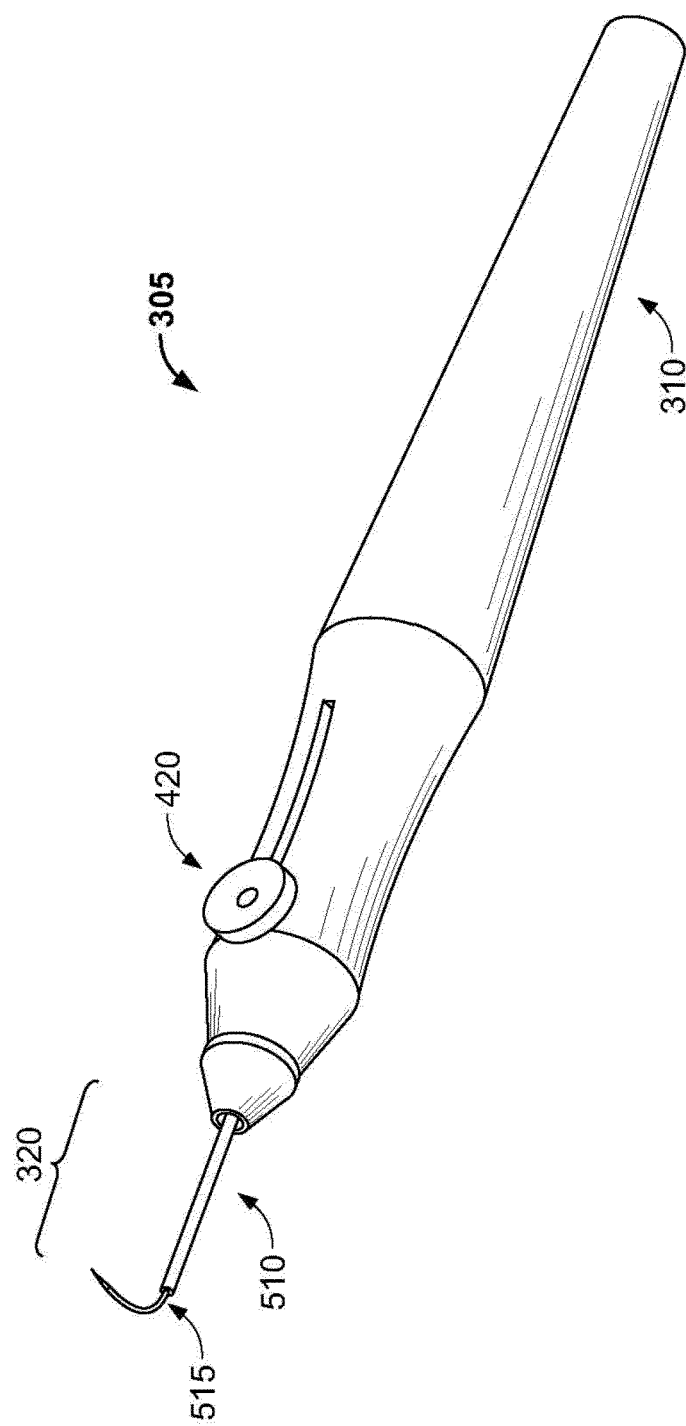
FIG. 3B shows another embodiment of a delivery system that can be used to deliver an implant into the eye.
Figure 3C:
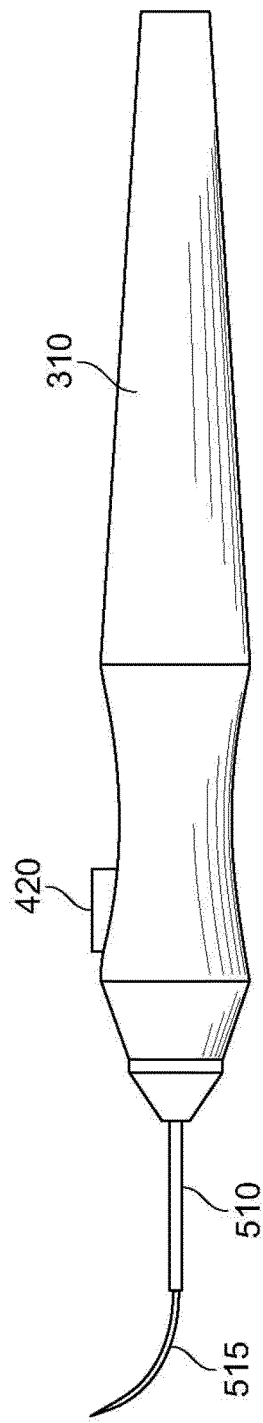
FIGS. 3C and 3D show the delivery system of FIG. 3B during actuation.
Figure 3D:
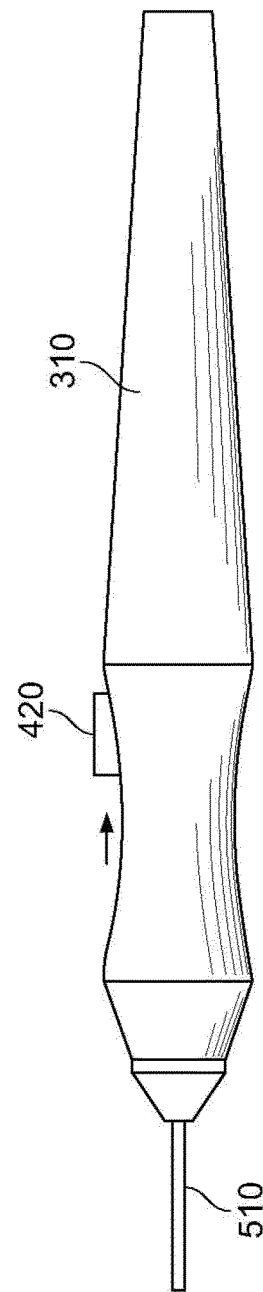

In an embodiment, a delivery system is used to deliver an implant 105 into the eye such that the implant 105 provides fluid communication between the anterior chamber and the suprachoroidal space. FIG. 3A shows an embodiment of a delivery system 305 that can be used to deliver the implant 105 into the eye. FIGS. 3B, 3C and 3D show another embodiment of a delivery system 305 that can be used to deliver the implant 105 into the eye. It should be appreciated that these delivery systems 305 are exemplary and that variations in the structure, shape and actuation of the delivery system 305 are possible.

The delivery system 305 generally includes a proximal handle component 310 and a distal delivery component 320. The proximal handle component 310 can include an actuator 420 to control the release of an implant from the delivery component 320 into the target location in the eye. The actuator 420 can vary in structure and mechanism and can include, for example, a button, switch, knob, slider, etc. The proximal handle component 310 also can include a channel 425 for insertion of a visualization system, such as a fiber optic image bundle 415, to be described in more detail below.

The delivery component 320 includes an elongate applier 515 that inserts longitudinally through the internal lumen of the implant 105 and a sheath 510 that can be positioned axially over the applier 515. The sheath 510 aids in the release of the implant 105 from the delivery component 320 into the target location in the eye. As best shown in FIGS. 3C and 3D, the actuator 420 can be used to control the applier 515 and/or the sheath 510. For example, the sheath 510 can be urged in a distal direction relative to the applier 515 to push the implant 105 off the distal end of the applier 515. Alternately, the sheath 510 can be fixed relative to the handle component 310. In this embodiment, the sheath 510 can act as a stopper that impedes the implant 105 from moving in a proximal direction as the applier 515 is withdrawn proximally from the implant 105 upon actuation of the actuator 420. In a first state shown in FIG. 3C, the applier 515 is extended distally relative to the sheath 310. Movement of the actuator 420, such as in the proximal direction, can cause the applier 515 to slide proximally into the sheath 510 as shown in FIG. 3D. This effectively disengages the implant 105 from the distal end of the applier 515 and releases the implant 105 in a controlled fashion such that the target positioning of the implant 105 within the suprachoroidal space is maintained.

Internal Implant Retention Layer

Figure 4E:
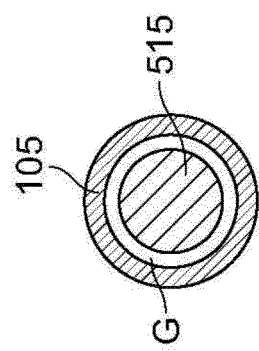
FIG. 4E is a cross-sectional view of an embodiment of a delivery system.
Figure 4F:
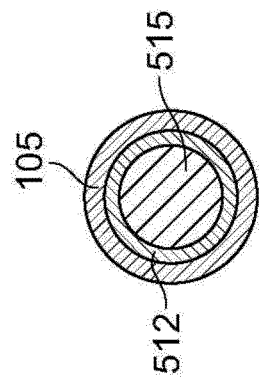
FIG. 4F is a cross-sectional view of the delivery system of FIG. 4A taken along line F-F.
Figures 4G, 4H, 4I, 4J:
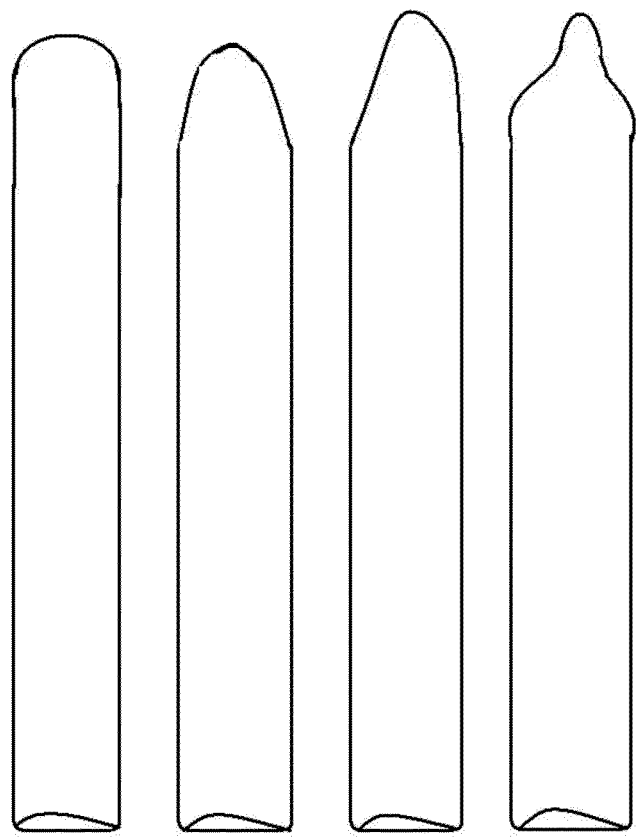
FIGS. 4G-4J are schematic views of a distal tip of an applier according to various embodiments.

The outer diameter of the applier 515 is generally smaller than the inner diameter of the implant 105 (i.e. the fluid channel) such that the implant 105 can be loaded onto the applier 515 such as by sliding the applier 515 into and through the internal lumen of the implant 105. In some instances, the outer diameter of the applier 515 can be significantly smaller thereby creating a gap G between the applier 515 and the implant 105 (see FIG. 4E). This gap G leaves room for adding a retention layer 512 or a retention coating to the delivery component 320 (see FIG. 4F). The retention layer 512 can act to retain the implant 105 on the applier 515 during blunt dissection and implantation to prevent the implant 105 from inadvertently falling off the applier 515 until it is delivered to the desired target location within the eye. An advantage of a retention layer 512 between the implant and the applier is the very low profile of the delivery system 305 and a user's improved ability to visualize each step of implantation. Retention layers added externally around the implant, in contrast, significantly increase the profile of the delivery device and negatively impact the user's ability to visualize the steps of delivery. External retention layers can also increase the size of the incision needed to insert the delivery device.

FIGS. 4A-4D show cross-sectional schematic views of an implant 105 mounted on a delivery portion 320 inserted from the anterior chamber into a region of the suprachoroidal space. The figures show an implant 105 mounted on the end of an applier 515, a sheath 510 sized and shaped to receive or abut a portion of the proximal end 125 of the implant 105, and a retention layer 512 providing an interference fit between the implant 105 and the applier 515. In this embodiment upon actuation the applier 515 slides in the proximal direction (arrow P) into the sheath 510. The proximal end 125 of the implant 105 abuts the distal edge of the sheath 510 to prevent the implant 105 from sliding in the proximal direction. This effectively disengages the implant 105 from the distal end of the applier 515 and controllably releases the implant 105 into a region of the suprachoroidal space SC. The retention layer 512 moves with the applier 515 such that the applier 515 and retention layer 512 are fully withdrawn into the sheath 510. It should be appreciated that the sheath 510 can also advanced distally over the applier 515 upon actuation to deliver the implant 105 into the suprachoroidal space.

The retention layer 512 can include, for example, a sleeve such as a shrink-to-fit tube that can be inserted over the applier 515. The retention layer 512 can also be inserted through the fluid pathway of the implant 105. The retention layer 512 can also include a coating of material, for example on the outer diameter of the applier 515 or on the inner diameter of the implant 105. The retention layer 512 can also serve to prevent tissue from jamming into the gap G between the applier 515 and implant 105, for example during insertion of the device through the iris root or the ciliary body.

The retention layer 512 can be a variety of materials. In an embodiment, the retention layer 512 can be a generally soft, elastomeric, compliant polymer. For example, the material of the retention layer 512 can include silicone, thermoplastic elastomers (HYTREL, RATON, PEBAX), certain polyolefin or polyolefin blends, elastomeric alloys, polyurethanes, thermoplastic copolyester, polyether block amides, polyamides (such as Nylon), block copolymer polyurethanes (such as LYCRA). Some other exemplary materials include fluoropolymer (such as FEP and PVDF), FEP laminated into nodes of ePTFE, acrylic, low glass transition temperature acrylics, and hydrogels. It should also be appreciated that stiffer polymers can be made to be more compliant by incorporating air or void volumes into their bulk, for example, PTFE and expanded PTFE.

Dissection Dynamics of Applier

As described above, the delivery component 320 can include an elongate applier 515. The shape, structure, materials and/or material properties of the applier 515 can be selected to optimize the gentle, blunt dissection between the tissue boundaries adjacent to the inner wall of the sclera and formation of the suprachoroidal space. The applier 515 can have a cross-sectional size and shape that complements the cross-sectional size and/or shape of the internal lumen of the implant 105 through which the applier 515 extends when the implant 105 is loaded thereon.

A variety of parameters including the shape, material, material properties, diameter, flexibility, compliance, precurvature and tip shape of the applier 515 can impact the performance of the applier 515 during gentle, blunt tissue dissection. The applier 515 desirably can penetrate certain tissues while avoids penetration of other tissues. For example, in an embodiment, it is desirable that the applier 515 be capable of penetrating the iris root or the ciliary body. The same applier 515 would beneficially be incapable of penetrating the scleral spur or inner wall of the sclera such that it can gently dissect between the tissue boundaries adjacent to the inner wall of the sclera. In an embodiment, the scleral spur can be penetrated during delivery. If penetration of the scleral spur does occur, penetration through the scleral spur can be accomplished in various manners. In one embodiment, a sharpened distal tip of the applier or the implant punctures, penetrates, dissects, pierces or otherwise passes through the scleral spur toward the suprachoroidal space. The crossing of the scleral spur or any other tissue can be aided such as by applying energy to the scleral spur or the tissue via the distal tip of the applier. The means of applying energy can vary and can include mechanical energy, such as by creating a frictional force to generate heat at the scleral spur. Other types of energy can be used, such as RF laser, electrical, etc.

The shape of the applier 515 along its long axis can be straight (as shown in FIG. 3A) or it can be can be curved along all or a portion of its length (as shown in FIGS. 3B, 3C and 3D) in order to facilitate proper placement. In the case of the curved applier 515, the radius of curvature can vary. For example, the applier 515 can have a radius of curvature of 3 mm to 50 mm and the curve can cover from 0 degrees to 180 degrees. In one embodiment, the applier 515 has a radius of curvature that corresponds to or complements the radius of curvature of a region of the eye, such as curvature of the inner wall of the sclera. For example, the radius of curvature can be approximately 11-12 mm. Moreover, the radius of curvature can vary moving along the length of the applier 515. There can also be means to vary the radius of curvature of portions of the applier 515 during placement.

The distal tip shape of the applier 515 can play a part in whether or not the applier 515 penetrates certain tissues. For example, the scleral wall is a tougher tissue than the ciliary body or the iris root and generally requires a sharp-tipped applier in order to be penetrated. The distal tip of the applier 515 can be sharp enough to penetrate the iris root or the ciliary body, but not so sharp (or sufficiently dull) so as not to easily penetrate the inner wall of the sclera. The tip shape of the applier 515 can vary. As shown in FIGS. 4G-4J, the distal tip of the applier 515 described herein can have a broad angle tip.

The tip shape can be symmetrical relative to a central, longitudinal axis of the applier, such as a hemispheric tip, blunt-tipped cone, rounded-off cone tip, etc. . . . The tip shape can also be asymmetrical such as a shovel or spade shape tip. In an embodiment the applier 515 has a blunt tip. The blunt or atraumatic tip shape aids in the gentle dissection between tissues, such as the sclera and the ciliary body and the sclera and the choroid if such dissection occurs.

The distal tip of the applier 515 can also be coated to reduce friction during dissection. In an embodiment, the distal tip of the applier 515 is coated with a hydrophilic coating such as HYDAK (Biocoat, Horsham, Pa.) or another slippery coating as is known in the art. A balance can be struck between the angle of the distal tip, the angle of approach to the dissection entry point and whether or not the tip is covered by a slippery coating such that the risk of penetrating certain tissues (i.e. inner wall of the sclera) is reduced while the ability to penetrate other tissues (i.e. iris root or ciliary body) is maintained.

In addition to tip shape, coatings and pre-curvature of the applier 515, specific dissection performance also depends in part on the compliance and flexibility of the applier 515. The compliance and flexibility of the applier 515 is generally a function of the material, material properties and diameter of the material selected for the applier. As mentioned above, it can be desirable to have an applier 515 that does not easily penetrate tissues such as the inner wall of the sclera. But it can also be desirable to have an applier 515 that can penetrate through other tissues such as the iris root or the ciliary body. Similarly, it can be desirable to have an applier 515 that can hug the curve of the inner scleral wall during blunt tissue dissection. The applier 515 described herein is designed such that it can penetrate tissues that the user wants to penetrate, but does not easily penetrate tissues that the user wants to avoid penetrating.

The outer diameter of the applier 515 can be selected and optimized based on the material and flexibility of the material used for the applier 515. An applier made of nitinol, for example, can have an outer diameter of about 0.009 inches. Nitinol is a superelastic metal that is quite bendable yet is stiff enough to be pushed through the iris root and the ciliary body to reach to and hug the curve of the inner scleral wall during blunt dissection along the boundary between the sclera and the adjacent tissues to the inner scleral wall. When combined with other features of the applier, for example a blunt tip, a nitinol applier having an outer diameter of about 0.009 inches can be used to gently dissect the tissue layers while avoiding tunneling or piercing one or both the inner scleral wall and choroid. Stainless steel spring wire is another material that could be used for the applier 515. Stainless steel wire is generally slightly stiffer than nitinol. Thus, the outer diameter of an applier made of stainless steel wire may need to be somewhat smaller than the outer diameter for an applier made of nitinol in order to achieve the same performance during blunt dissection. In an embodiment, the applier has an outer diameter of about 0.0017 inches. It should be appreciated that for a given material's flexibility, the optimum outer diameter of the applier can be determined and extrapolated for an applier of a different material having a different degree of flexibility. Other materials considered for the applier 515 include compliant flexible wires made from a polymer or a polymer composite wire reinforced with high-strength fibers.

Visualization System

Challenges exist with respect to visualization during implantation procedures such as described herein. Structures near the angle of the eye are hidden from ordinary or direct view because of total internal reflection of light rays emanating from the angle structures. Typically a gonioscope or viewing lens is needed to view the angle of the eye, for example during implantation of a device into the suprachoroidal space. The delivery systems described herein need not be used in conjunction with a gonioscope or viewing lens. The delivery systems described herein can include an internal visualization system that eliminates the need for a gonioscope.

FIGS. 5A-5D and 6A-6B show an embodiment of a delivery system 305 having an internal imaging system 430. The fiber optic image bundle and lens imaging system is very tiny and has a low profile such that the overall low profile of the delivery system 305 is maintained and trauma to the eye is minimized. The size and profile of the fiber optic image bundle 415 is such that it maintains the advantages described above with respect to the low profile applier and internal retention system. In an embodiment, the fiber optic image bundle 415 is less than 0.5 mm in diameter. In an embodiment, the fiber optic image bundle 415 can include a coherent fiber optic bundle 705 surrounded by a fiber optic sheath 710 or cladding.

As described above, the delivery system 305 can include a channel 425 in its handle component 310 through which a tiny fiber optic image bundle 415 can be inserted providing visualization to the delivery component 320. The fiber optic image bundle 415 can be inserted into the channel 425 through an opening near the proximal end of the handle 310 component, exit through another opening of the channel 425 near the distal end of the handle 310. The fiber optic image bundle 415 can emerge from the distal end of the handle 310 under the applier shaft such that it aligns coaxially with or parallel and adjacent to the implant 105 and applier 515.

It should be appreciated that the fiber optic image bundle 415 can reversibly couple with the handle 310. Just as a surgeon can insert the fiber optic image bundle 415 through the channel 425 in the handle 310 for use, the surgeon can also withdraw the fiber optic image bundle 415 from the channel 425 and handle 310 when not in use or when use of an imaging system is not desired. The reversible connection of the fiber optic image bundle 415 through the channel 425 provides a surgeon with a good deal of flexibility in that the user decides whether or not to use the visualization system during implantation procedures. The delivery device can be manufactured and provided to a surgeon with the fiber optic image bundle already installed through the handle 310 of the device. In this embodiment, the surgeon can still remove the fiber optic image bundle 415 from the handle 310 if the surgeon chooses. Alternatively, the delivery device can be manufactured as part of a kit that includes a fiber optic image bundle 415 that is separate from the handle 310 that can be readily and reversibly inserted through the channel 425 to the discretion of the surgeon.

Still with respect to FIGS. 5A-5D, 6A and 6B the fiber optic image bundle 415 can be fed through the channel 425 until its distal tip is positioned a distance proximal to the distal tip of the applier 515 where the implant 105 is mounted on the applier 515 providing an objective angle view to the surgeon. The fiber optic image bundle 415 can extend towards the distal tip of the applier 515 (see FIG. 5C), for example such that it is positioned a few millimeters away from the distal tip of the applier 515. The fiber optic image bundle 415 can be positioned near the distal tip of the applier 515 such that it provides adequate visualization and, optionally, internal illumination, at the implantation site, but is not positioned so close to the distal tip that it interferes with the surgical field where the implant 105 is to be inserted and the gentle dissection of the tissues is desired. The visual perspective from the fiber optic image bundle 415 positioned a few millimeters back from the distal tip of the applier 515 can provide an objective angle, "headlight" type field of view for the surgeon to visualize the implantation procedure. In an embodiment, the distal tip of the fiber optic image bundle 415 can be positioned between about 3-20 mm from the distal tip of the applier 515. In another embodiment, the fiber optic image bundle 415 can be positioned at least about 9 mm from the distal tip of the applier 515. In another embodiment, the distal tip of the fiber optic image bundle 415 can be positioned at least about 6 mm from the distal tip of the applier 515.

Figure 5A:
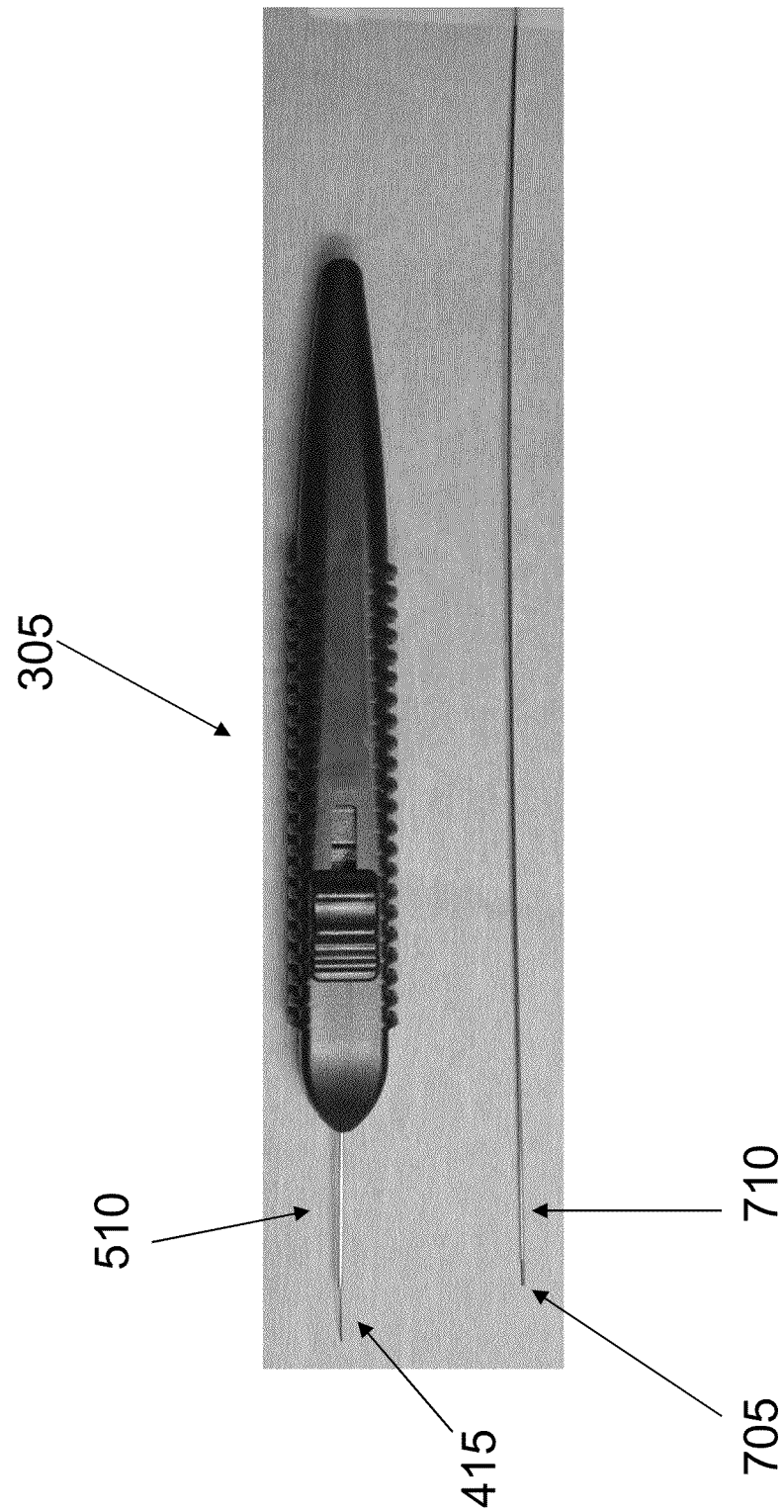
Figure 5D:
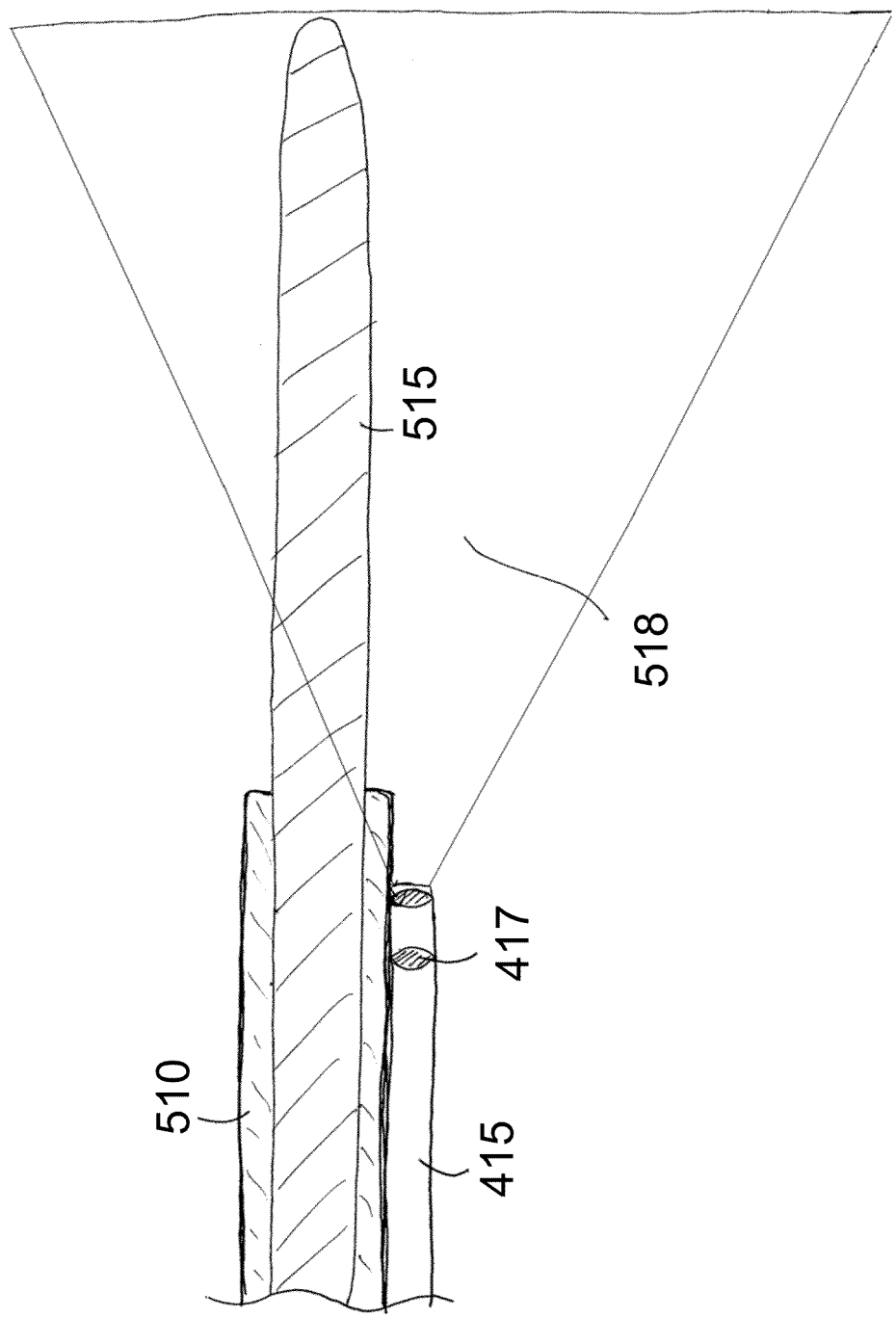

FIG. 5D shows a schematic, enlarged view of the delivery and visualization system. The fiber optic image bundle 415 is shown positioned external to the sheath 510 and positioned several millimeters proximal to the distal tip of the applier 515. The applier 515 although shown straight can have a slightly curved distal tip near where it abuts the tissues to be bluntly dissected. It should be appreciated that the distal tip of the applier remains within the visual field of the image bundle 415 regardless of whether or not the distal tip is curved. The fiber optic image bundle 415 can be a coherent bundle of fibers and can include one or more lenses 417 near the tip of the image bundle 415. In an embodiment, two lenses 417 can be separated from one another to provide a gathering field of view 518, for example, approximately 65 degrees from the aqueous side of the distal tip of the applier 515.

Figure 6A:
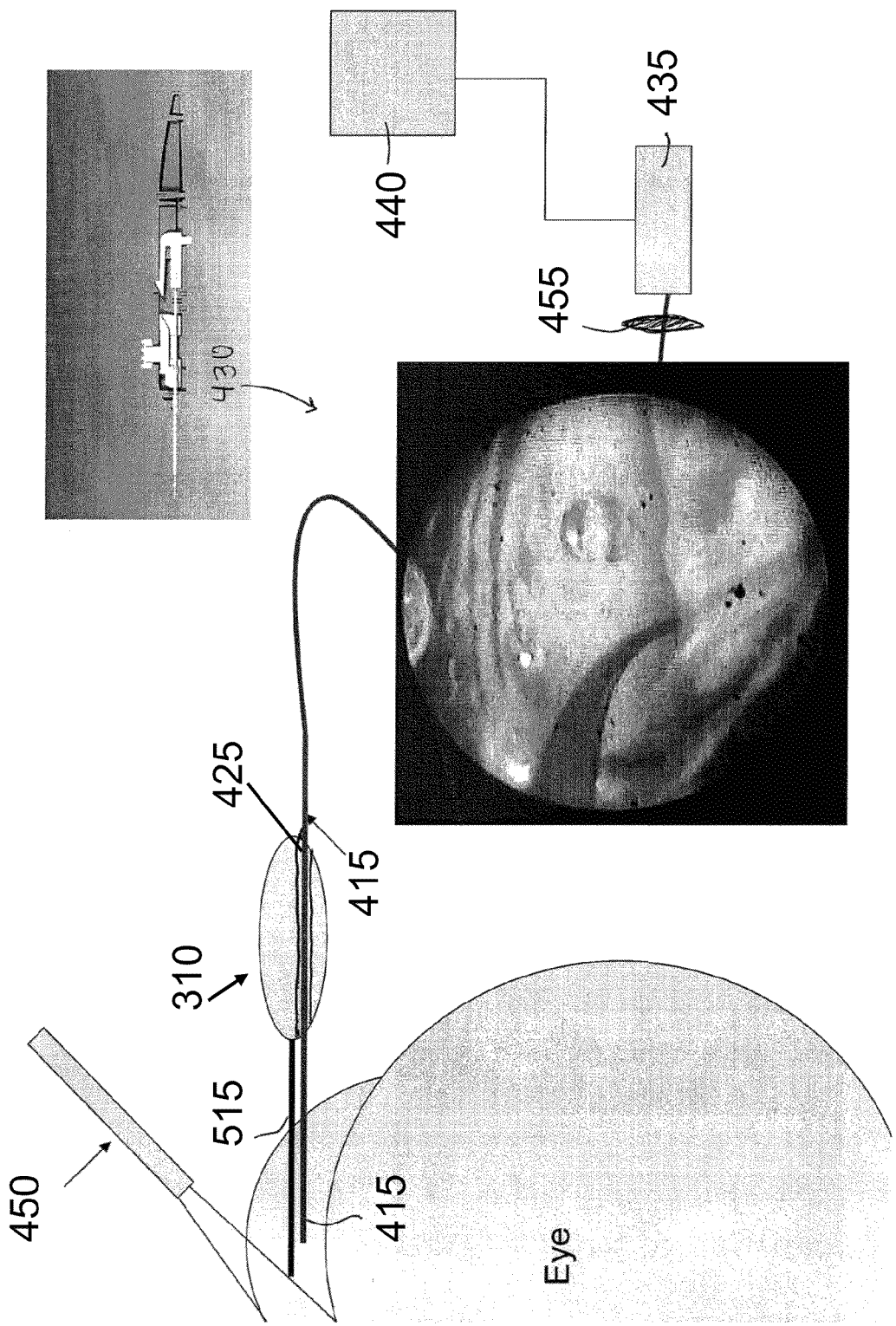
FIG. 6A shows an embodiment of a fiber optic visualization and delivery system.
Figure 6B:
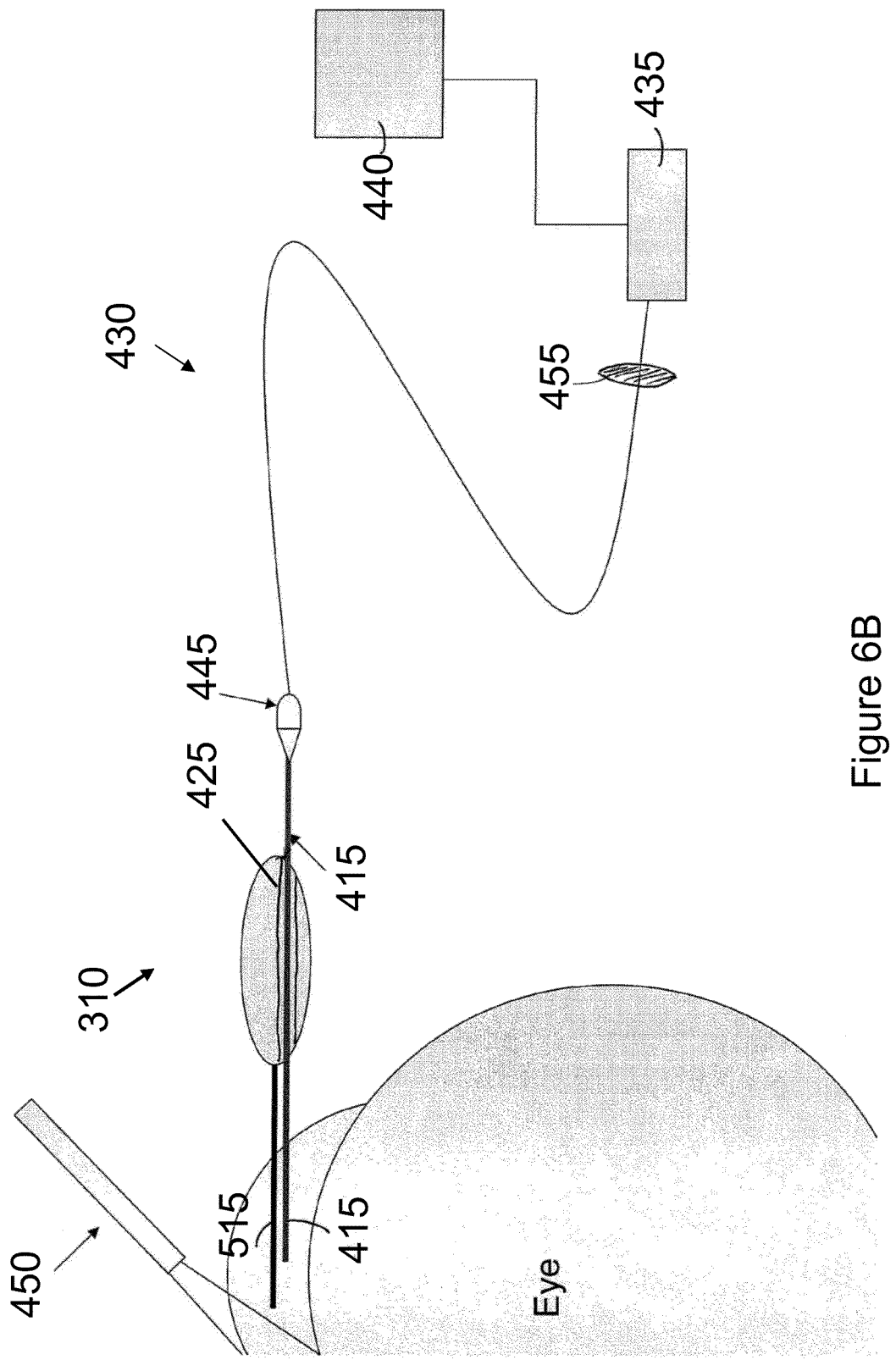
FIG. 6B shows another embodiment of a fiber optic visualization and delivery system.

As best shown in FIG. 6A-6B, the imaging system 430 can include an image capture device 435. The image capture device 435 can be, for example, a camera, a digital microscope (for example, a handheld USB digital microscope, such as a Dino-Lite microscope) or a silicon-based CCD (charge-coupled device) digital color video camera and the like. The image capture device 435 can capture images in the infrared (IR) spectrum of light, as will be described in more detail below. The imaging system 430 can also include a filtering element 455, such as a narrow band pass filter that filters out the visible light from the image capture device 435 to optimize the IR image captured.

The imaging system 430 can also include an image sensor 445 (see FIG. 6B). The image sensor 445 can be a low mass type of camera such as a CMOS (complementary metal oxide semiconductor) chip, for example an OmniVision CMOS CameraChip™ image sensor (OmniVision, Santa Clara, Calif.). The light gathered from the image bundle 415 can be converted by the image sensor 445 into an electrical signal used by an evaluation module (not shown). The imaging system 430 can also include a data processing device 440 such as a PC computer/monitor for collecting, recording and/or viewing image data. In an embodiment, image data (including still images and/or video images) captured by the image capture device 435 or image sensor 445 can be processed directly by the data processing devices 440. The image data can be visualized by the surgeon in real-time such as on a computer monitor for use during a procedure. The surgeon can simultaneously view image data, for example, through a surgical microscope (not shown) aided by an external illumination source in the visible light spectrum as described above. The data processing devices 440 can be adapted to execute image analysis software and can include storage means for recording image data.

The imaging system 430 can also include a miniature projector system, such as a DLP® Pico™ Projector Kit (Texas Instruments, Dallas, Tex.). Image data (including still images and/or video images) captured by the image capture device 435 or image sensor 445 can be projected onto a small screen that can be positioned near the surgical field or within one of the oculars of the instrument such that the surgeon can view the images projected onto the screen without having to look up from the surgical microscope during the procedure. The projection screen size can vary depending on the configuration used. For example, the projection screen can be between about 6" to about 60". The projector system can be used in place of a larger video monitor or display that can be mounted inside the operating room, but away from the patient and the surgical field.

As mentioned, the visualization system can also include an illumination source 450. The illumination source 450 can be used for the image capture of the surgical field with an imaging system. The illumination source can be internal and combined with the fiber optic image bundle 415 such that it is inserted through the same incision as the applier 515 and implant 105. It should be appreciated, however that an internal illumination source can have a negative impact on the overall diameter of the delivery component 320. For example, a fiber optic image bundle 415 is generally about 0.5 mm in diameter. Adding an illumination source 450 to the fiber optic image bundle 415 plus the cladding between the light source and the image bundle can increase the diameter to approximately 1.0 mm, necessitating a larger incision in the eye to insert the delivery component 320. Increased profile of the delivery component can also impact the surgeon's view of the surgical field. Thus, the illumination source 450 can also be separate from the delivery component 320 and inserted through a separate incision in order to maintain overall small incision size.

In another embodiment the illumination source 450 can be external (see, for example FIGS. 6A and 6B). The external illumination source 450 can include an external IR illumination source such as an IR flood lamp, IR light-emitting diode (LED) or IR LED array. In an embodiment, a white light external illumination source can be used such as an incandescent or a white light LED.

The delivery system can use an illumination source 450 for the image capture of the surgical field that is independent of the illumination source for the surgeon's view of the surgical field. The illumination source for image capture of the surgical field with an IR imaging system 430 (to be described in more detail below) can be near infrared (IR) light, for example in the 700-1200 nm (0.7-1.2 µm) range. In contrast, the illumination source for the surgeon's view of the surgical field can be in the visible light spectrum. The modulation controls for the IR source can be independent of the modulation controls for the white light source. Independent illumination modulations between white light and IR light allow a surgeon to increase the amount of IR light needed to capture adequate images with the imaging system 430, while the white light illumination source can be kept at a comfortable level for both the surgeon and the patient. The image quality of the surgical field using the imaging system 430 can be optimized (such as by increasing the amount of IR illumination) without negatively impacting the surgeon's view of the same region using visible light. The dual illumination system of both IR-visible light includes independent modulation controls such that one imaging system (i.e. IR imaging system) does not impact the image achieved by the other imaging system (i.e. surgeon's eyes).

Methods of Implant Delivery

A method of delivering and implanting the implant into the eye is now described. In general, one or more implants 105 can be slidably mounted on and implanted in or near the suprachoroidal space using a delivery system as described herein. The mounting of the implant on the applier of the delivery system can be aided by a retention layer (or a retention coating on the applier or the internal walls of the implant) that reversibly retains the implant on the tip of the applier while still maintaining a flexible and low profile applier as described above. The retention layer can be used to prevent the implant from falling off the applier inadvertently during delivery until the user actuates the delivery component and effects controlled release of the implant from the applier 515, for example, upon proximal withdrawal of the applier 515. The implant 105 can then be secured in the eye so that it provides fluid communication between the anterior chamber and the suprachoroidal space.

Each step of implantation can be continually visualized in real-time using the fiber optic image bundle 415 positioned near the distal end of the applier 515 and images of the structures and devices within the eye can be captured by the imaging system 430. Simultaneously, the images of the structures and devices within the eye can be viewed by a surgeon such as through a surgical microscope or a computer monitor receiving input from the imaging system 430. As described above, the independent illumination sources in the IR and white light spectrums can be independently controlled to allow the surgeon to increase IR illumination in order to obtain the best IR image through the imaging system 430 without affecting the physician's own view using the visible light illumination source. Visualization can occur continuously during implantation or other procedures without the need for re-positioning or removing one or more components of the imaging systems and without the need for viewing through a goniolens.

Figure 7:
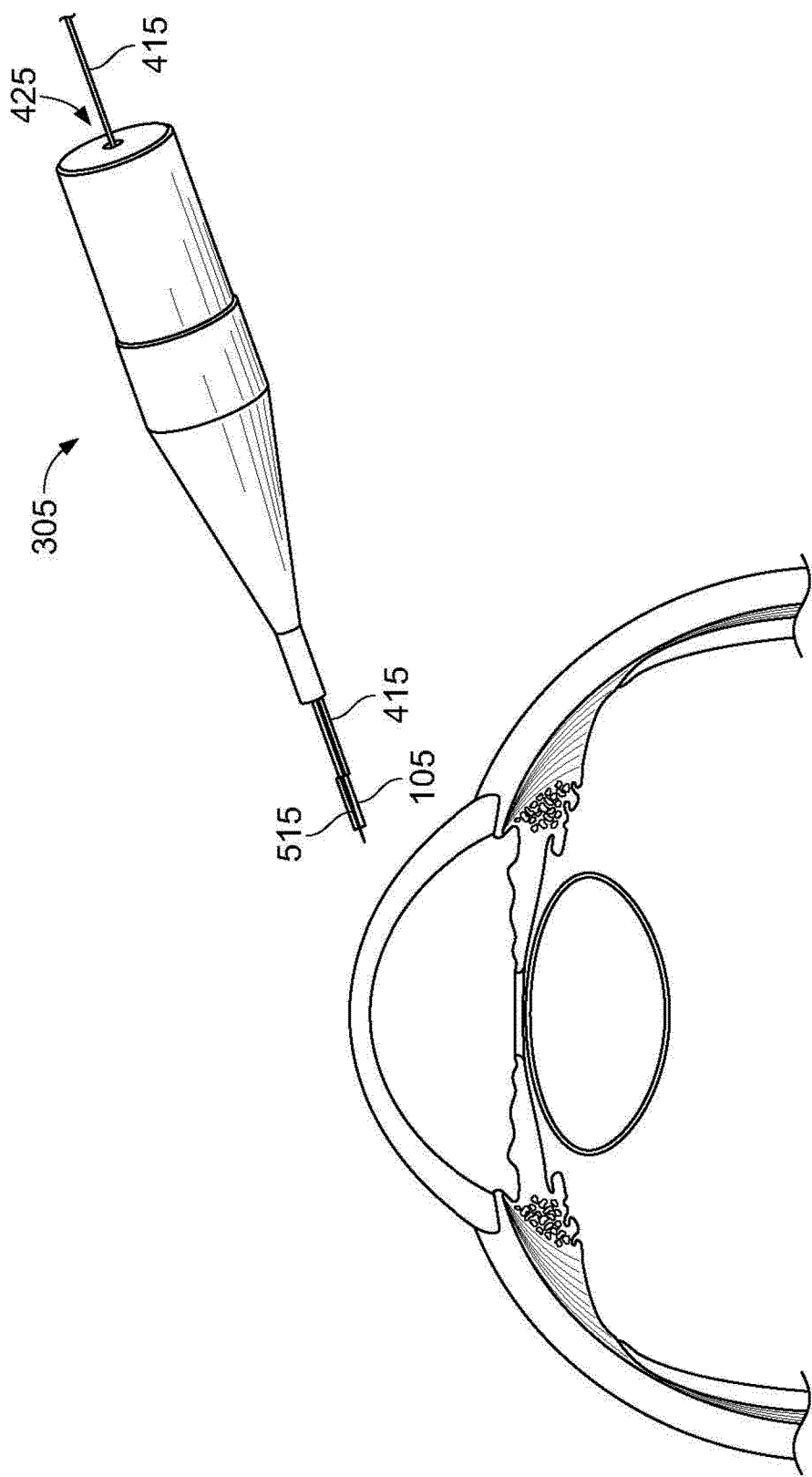
FIG. 7 shows a schematic of the fiber optic visualization and delivery system positioned for penetration into the eye.

With reference to FIG. 7, the applier 515 is positioned such that the distal tip, the implant 105 and fiber optic image bundle 415 can penetrate through a small, corneal incision to access the anterior chamber. The fiber optic image bundle 415 can be inserted through the same incision in the cornea as the applier 515 with the implant 105 loaded at its distal tip. This provides the advantage that only one incision is required to deliver the implant and visualize the implantation procedure. In this regard, the single incision can be made in the eye, such as within the limbus of the cornea. In an embodiment, the incision is very close to the limbus, such as either at the level of the limbus or within 2 mm of the limbus in the clear cornea. The applier 515 can be used to make the incision or a separate cutting device can be used. For example, a knife-tipped device or diamond knife can be used to initially enter the cornea. A second device with a spatula tip can then be advanced over the knife tip wherein the plane of the spatula is positioned to coincide with the dissection plane.

The corneal incision has a size that is sufficient to permit passage of the implant on the applier as well as the fiber optic image bundle therethrough. In an embodiment, the incision is about 1 mm in size. In another embodiment, the incision is no greater than about 2.85 mm in size. In another embodiment, the incision is no greater than about 2.85 mm and is greater than about 1.5 mm. It has been observed that an incision of up to 2.85 mm is a self-sealing incision. For clarity of illustration, the Figures are not to scale.

After insertion through the incision, the applier 515 can be advanced into the anterior chamber along a pathway that enables the implant 105 to be delivered to a position such that the implant 105 provides a flow passageway from the anterior chamber to the suprachoroidal space. With the delivery portion 320 positioned for approach, the applier 515 can be advanced further into the eye such that the blunt distal tip of the applier 515 and/or the implant 105 penetrates the tissue at the angle of the eye, for example, the iris root or a region of the ciliary body or the iris root part of the ciliary body near its tissue border with the scleral spur, to be discussed in more detail below.

The scleral spur is an anatomic landmark on the wall of the angle of the eye. The scleral spur is above the level of the iris but below the level of the trabecular meshwork. In some eyes, the scleral spur can be masked by the lower band of the pigmented trabecular meshwork and be directly behind it. The applier can travel along a pathway that is toward the angle of the eye and the scleral spur such that the applier passes near the scleral spur on the way to the suprachoroidal space, but does not necessarily penetrate the scleral spur during delivery. Rather, the applier 515 can abut the scleral spur and move downward to dissect the tissue boundary between the sclera and the ciliary body, the dissection entry point starting just below the scleral spur near the iris root IR or the iris root portion of the ciliary body. In another embodiment, the delivery pathway of the implant intersects the scleral spur. In an embodiment, the scleral spur can be penetrated during delivery. If penetration of the scleral spur does occur, penetration through the scleral spur can be accomplished in various manners. In another embodiment, a sharpened distal tip of the applier or the implant can puncture, penetrate, dissect, pierce or otherwise passes through the scleral spur toward the suprachoroidal space. The crossing of the scleral spur or any other tissue can be aided such as by applying energy to the scleral spur or the tissue via the distal tip of the applier. The means of applying energy can vary and can include mechanical energy, such as by creating a frictional force to generate heat at the scleral spur. Other types of energy can be used, such as RF laser, electrical, etc.

The applier 515 can approach the angle of the eye from the same side of the anterior chamber as the deployment location such that the applier 515 does not have to be advanced across the iris. Alternately, the applier 515 can approach the angle of the eye from across the anterior chamber AC such that the applier 515 is advanced across the iris and/or the anterior chamber toward the opposite angle of the eye. The applier 515 can approach the angle of the eye along a variety of pathways. The applier 515 does not necessarily cross over the eye and does not intersect the center axis of the eye. In other words, the corneal incision and the location where the implant is implanted at the angle of the eye can be in the same quadrant (if the eye is viewed from the front and divided into four quadrants). Also, the pathway of the implant from the corneal incision to the angle of the eye ought not to pass through the centerline of the eye to avoid interfering with the pupil.

Figure 8:
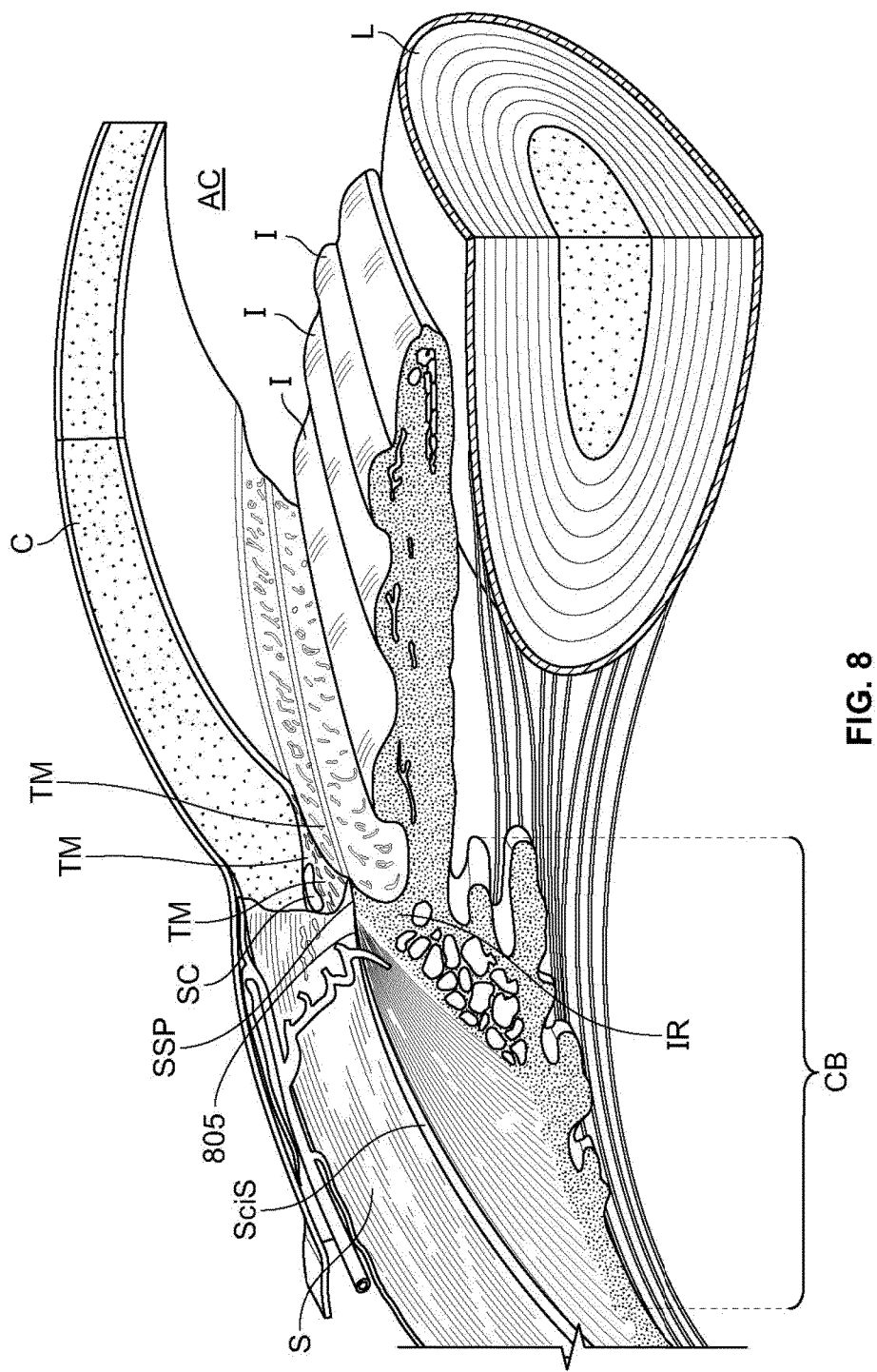
FIG. 8 shows an enlarged view of a portion of the anterior region of the eye in cross-section.

FIG. 8 shows an enlarged view of the anterior region of the eye showing the anterior chamber AC, the cornea C, the iris I, and the sclera S. The implant 105 mounted on the applier 515 and fiber optic image bundle 415, can approach the angle of the eye from the anterior chamber. They move along a pathway such that the dissection entry point of the distal tip of the applier 515 can penetrate the iris root IR or the iris root portion of the ciliary body CB near its junction with the scleral spur SSp. Other penetration points near the angle of the eye are also considered herein. The surgeon can rotate or reposition the handle of the delivery device in order to obtain a proper approach trajectory for the distal tip of the applier 515, as described in further detail below.

The fiber optic image bundle 415 positioned proximal to the implant 105 on the applier 515 provides continuous visualization during delivery of the implant 105 to a position that communicates with the suprachoroidal space SChS. The fiber optic image bundle 415 can be positioned a distance proximal to the distal tip of the applier 515 and provide an objective angle view to the physician. Although the fiber optic image bundle 415 can be positioned near the distal tip to provide an objective angle view of the implantation site, it does not interfere with the surgical field where the implant 105 is to be inserted. In an embodiment, the fiber optic image bundle 415 can be between about 3-20 mm from the distal tip of the applier 515. In another embodiment, the fiber optic image bundle 415 can be at least about 9 mm from the distal tip of the applier 515. In another embodiment, the fiber optic image bundle 415 can be at least about 6 mm from the distal tip of the applier 515.

The applier 515 with the implant 105 positioned thereupon can be advanced through tissues near the angle of the eye, such as the iris root IR, the ciliary body or the iris root portion of the ciliary body. As the applier 515 is advanced it can penetrate an area of fibrous attachment 805 between the scleral spur and the ciliary body (see FIG. 8). This area of fibrous attachment 805 can be approximately 1 mm in length. Once the distal tip of the applier 515 penetrates and is urged past this fibrous attachment region 805, it then can more easily cause the sclera S to peel away or otherwise separate from the ciliary body and choroid as it follows the inner curve of the sclera to form the suprachoroidal space SChS. As described above, a combination of the applier's tip shape, material, material properties, diameter, flexibility, compliance, coatings, pre-curvature etc. make it more inclined to follow an implantation pathway that mirrors the curvature of the inner wall of the sclera and between tissue layers such as between the sclera S and the ciliary body, and between the sclera and the choroid.

The applier 515 can be continuously advanced into the eye, for example approximately 6 mm. The dissection plane of the applier 515 can follow the curve of the inner scleral wall such that the implant 105 mounted on the applier 515, for example after penetrating the iris root or the iris root portion of the ciliary body, can bluntly dissect the boundary between tissue layers of the scleral spur SSp and the ciliary body CB such that a distal region of the implant extends through the suprachoroidal space SchS and then, further on, is positioned between the tissue boundaries of the sclera and the choroid forming the suprachoroidal space. In an embodiment, the implant 105 is positioned such that it does not extend past the scleral spur SSp far enough to reach or otherwise contact the choroid. That is, the distal end of the implant does not reach and cannot contact the choroid. In another embodiment, the implant 105 extends sufficiently past the scleral spur SSp such that it is positioned between the tissue boundaries of the sclera and the choroid.

Figure 9:
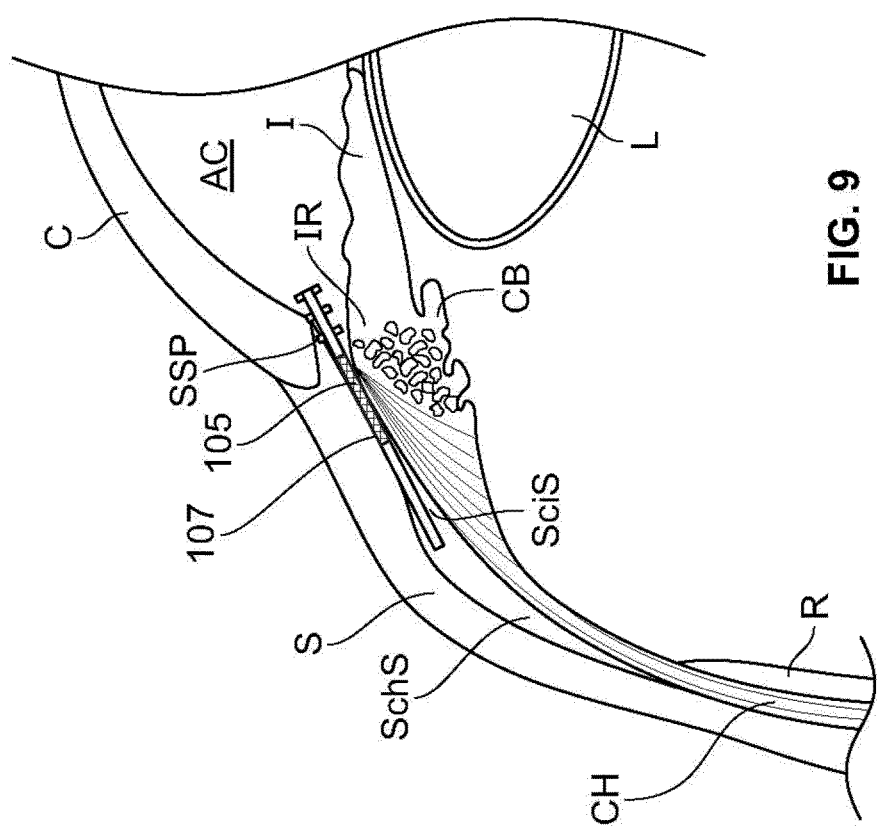
FIG. 9 shows an implant positioned within the eye.

FIG. 9 shows the implant 105 positioned within the suprachoroidal space SChS. For clarity of illustration, FIG. 9 does not show the implant 105 mounted on the applier 515, although the implant 105 is mounted on the applier 515 during delivery. A first portion of the implant 105 can be positioned within the suprachoroidal space and a second portion of the implant 105 can remain within the anterior chamber AC. In one embodiment, at least 1 mm to 2 mm of the implant (along the length) remains in the anterior chamber AC.

The implant 105 can be positioned in the eye so that a portion of the implant is sitting on top of the ciliary body CB. The ciliary body CB can act as a platform off of which the implant 105 can cantilever into the suprachoroidal space SChS. The implant 105 can have a relative stiffness such that, when implanted, the implant 105 deforms at least a portion of the tissue adjacent the suprachoroidal space to take on a shape that is different than the natural curvature. In this manner, the implant 105 can lift or "tent" the sclera S outward such that the suprachoroidal space SchS is formed around the distal end of the implant 105. The tenting of the sclera S as shown in FIG. 9 has been exaggerated for clarity of illustration. It should be appreciated that the actual contour of the tented region of tissue may differ in the actual anatomy. Whether the distal end of the implant 105 is positioned between the sclera and the ciliary body or the sclera and the choroid, the implant 105 can act as a flow pathway between the anterior chamber AC and the suprachoroidal space SchS without blockage of the outflow pathway by surrounding tissues such as the sclera or the choroid. As mentioned, in an embodiment the distal end of the implant 105 does not extend far enough to reach the choroid. In another embodiment, the distal end of the implant 105 reaches the choroid and may contact the choroid.

Once properly positioned, the implant 105 can then be released. The implant 105 can be released for example by withdrawing the applier 515 such that the implant 105 is effectively disengaged in a controlled manner from the tip of the applier 515 with the sheath 510 (for example via the manner described above with reference to FIGS. 4A-4D). A retention layer 512 can optionally be used to assist in retaining the implant 105 on the applier 515 during the steps of delivery. However, the relationship between the retention layer 512 and the implant 105 is readily reversible such that the applier 515 and retention layer 512 can be withdrawn into the sheath 510 to controllably release the implant 105 from the tip of the applier upon arrival at the target location within the eye.

The implant 105 can include one or more structural features that aid to anchor or retain the implant 105 in the target region in the eye. The structural features can include flanges, protrusions, wings, tines, or prongs, and the like that can lodge into the surrounding eye anatomy to retain the implant 105 in place and prevent the implant 105 from moving further into the suprachoroidal space SchS. The structural features also provide regions for areas of fibrous attachment between the implant 105 and the surrounding eye anatomy. FIG. 9 illustrates schematically an approximately 1 mm circumferential band 107 of the implant 105 near the junction of the iris root and the scleral spur along the inside of the scleral wall toward the back of the eye at which fibrous attachment can occur. Fibrous attachment can result, for example, from endothelial cell growth in, around and/or between retention features of the implant 105. In addition, a small amount of scaring in and around an area of fibrous tissue attachment between the scleral spur and the ciliary body in the region of the iris root portion of the ciliary body can provide for additional fixation to prop up the implant in its target location.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A system for delivering an ocular implant having a fluid channel, the system comprising:
a delivery device comprising:
a handle component having a proximal end, a distal end; and
a flexible wire coupled to the handle and insertable through a fluid channel of an ocular implant; and
a retention element on the flexible wire, the retention element providing an interference fit between an implant and the flexible wire when an implant is inserted on the flexible wire.

2. The system of claim 1, further comprising a fiber optic image bundle reversibly insertable through the handle such that the fiber optic image bundle extends to a region proximal to a distal tip of the flexible wire.

3. The system of claim 2, further comprising an illumination source that emits infrared light selected from the group comprising an infrared LED and an infrared flood lamp.

4. The system of claim 3, wherein the illumination source is external to the fiber optic image bundle.

5. The system of claim 3, further comprising a second illumination source.

6. The system of claim 5, wherein the second illumination source emits visible light selected from the group comprising white incandescent light, white LED and fiberoptic white light.

7. The system of claim 5, further comprising a first mechanism configured to control the first illumination source and a second mechanism configured to control the second illumination source, wherein the second illumination source control mechanism adjusts the second illumination source independent of the first illumination source control mechanism and the first illumination source.

8. The system of claim 3, further comprising a narrow band pass filter.

9. The system of claim 3, further comprising an imaging device configured to capture image data in the form of video images, still images or both.

10. The system of claim 9, wherein the imaging device is selected from the group comprising a hand-held digital microscope, a digital camera, a CCD video camera, a low mass camera, and a CMOS chip.

11. The system of claim 9, wherein the imaging device communicates the image data to a digital projector configured to project images in real-time to a small projector screen displayed near a patient's eye.

12. The system of claim 2, wherein the region proximal to the distal tip of the flexible wire is between about 3 and 20 millimeters proximal to the distal tip of the flexible wire.

13. The system of claim 2, wherein the fiber optic image bundle further comprises one or more lenses.

14. The system of claim 2, wherein the fiber optic image bundle provides an objective angle view of at least about 65 degrees.

15. The system of claim 1, further comprising the implant comprising an elongate member having a flow pathway, at least one inflow port communicating with the flow pathway, and an outflow port communicating with the flow pathway, wherein the elongate member is adapted to be positioned in an eye such that the inflow port communicates with an anterior chamber and the outflow port communicates with a suprachoroidal space.

16. The system of claim 15, wherein the elongate member is positioned into a suprachoroidal space without use of a goniolens.

* * * * *